(12) United States Patent
Quirno

(10) Patent No.: US 8,414,593 B2
(45) Date of Patent: Apr. 9, 2013

(54) SPINAL MEASURING DEVICE AND DISTRACTOR

(75) Inventor: Martin Quirno, New York, NY (US)

(73) Assignee: Q-Spine, LLC, New York, NY (US)

( * ) Notice: Subject to any disclaimer, the term of this patent is extended or adjusted under 35 U.S.C. 154(b) by 0 days.

(21) Appl. No.: 13/315,070

(22) Filed: Dec. 8, 2011

(65) Prior Publication Data

US 2012/0123426 A1    May 17, 2012

Related U.S. Application Data

(62) Division of application No. 12/273,999, filed on Nov. 19, 2008.

(60) Provisional application No. 61/080,030, filed on Jul. 11, 2008.

(51) Int. Cl.
| | |
|---|---|
| *A61B 17/58* | (2006.01) |
| *A61B 17/60* | (2006.01) |
| *A61F 2/00* | (2006.01) |

(52) U.S. Cl.
USPC ........................................... 606/90; 606/102

(58) Field of Classification Search ............ 606/57, 606/58, 86 A, 86 B, 90, 102, 105
See application file for complete search history.

(56) References Cited

U.S. PATENT DOCUMENTS

| | | | |
|---|---|---|---|
| 3,872,590 | A | 3/1975 | Hill |
| 4,621,250 | A | 11/1986 | Echasseriau et al. |
| 6,227,081 | B1 | 5/2001 | Bally et al. |
| 6,261,296 | B1 | 7/2001 | Aebi et al. |
| 6,984,993 | B2 | 1/2006 | Ariav |
| 7,189,234 | B2 | 3/2007 | Zucherman et al. |
| 2003/0226272 | A1 | 12/2003 | Finefield |
| 2004/0059261 | A1 | 3/2004 | Grinberg |
| 2004/0116835 | A1 | 6/2004 | Holmes |
| 2004/0133132 | A1 | 7/2004 | Chappuis |
| 2004/0249388 | A1 | 12/2004 | Michelson |
| 2004/0267279 | A1 * | 12/2004 | Casutt et al. .................. 606/104 |
| 2005/0080425 | A1 | 4/2005 | Bhatnagar et al. |
| 2005/0159756 | A1 | 7/2005 | Ray |
| 2005/0203532 | A1 | 9/2005 | Ferguson et al. |
| 2006/0004380 | A1 | 1/2006 | DiDomenico et al. |

(Continued)

OTHER PUBLICATIONS

ProDisc-L Total Disc Replacement, Technique Guide, Synthes Spine (Sep. 2006).

(Continued)

*Primary Examiner* — Andrew Yang
*Assistant Examiner* — Diana S Jones
(74) *Attorney, Agent, or Firm* — Weitzman Law Offices, LLC

(57) ABSTRACT

A device for determining an optimal size of an intervertebral implant, comprising movable posterior and anterior rods, each rod operatively connected to a pair of posterior and anterior distracting members, respectively. Each pair is movable in opposing radial directions in response to longitudinal rotation of the posterior and anterior rods, and has marks corresponding to the distance the distracting members have moved for the purpose of measuring posterior and anterior disc height. A position indicator allows measurement of longitudinal distance between the longitudinally movable posterior and anterior rods. The device further comprises load sensor plates movable in response to movement of the distracting members, first and second handles pivotally connected to the load sensor plates, a protractor disposed relative to the handles, allowing measurement of an angle between the first and second handles, and a transducer for measuring force applied during distraction.

11 Claims, 2 Drawing Sheets

U.S. PATENT DOCUMENTS

2006/0074431 A1* 4/2006 Sutton et al. .................. 606/90
2007/0209222 A1 9/2007 Fischer et al.
2007/0260260 A1 11/2007 Hahn et al.
2008/0082169 A1 4/2008 Gittings et al.

OTHER PUBLICATIONS

Burt Yaszay, MD, et al., Effect of Intervertebral Disc Height on Postoperative Motion and Outcomes After ProDisc-L Lumbar Disc Replacement, SPINE, vol. 33, No. 5, pp. 508-512 (2008).

* cited by examiner

SPINAL MEASURING DEVICE AND DISTRACTOR

CROSS-REFERENCE TO RELATED APPLICATION

This application is a divisional application of U.S. patent application Ser. No. 12/273,999, filed on Nov. 19, 2008, which claims the benefit of U.S. Provisional Application No. 61/080,030, filed Jul. 11, 2008, the entire disclosures of which are incorporated herein by reference.

FIELD

This application relates generally to surgical measuring devices, and more particularly, to an intervertebral measuring device for selecting an optimal size implant.

BACKGROUND

Chronic lower back pain caused by degenerative disc disease is one of the leading causes of disability in adults. Intervertebral disc degeneration can occur as part of the normal aging process in which the nucleus of the disc dehydrates, reducing the shock absorbing capability of the disc. Patients who fail to obtain adequate pain relief from non-surgical treatment (e.g., rest, pain medication, physical therapy, exercise, epidural steroid injections, chiropractic manipulation, ultrasound, massage, orthotics, etc.) may require spinal surgery to alleviate discogenic pain and disability.

One method of treating degenerative disc disease is spinal fusion or arthrodesis surgery in which the affected vertebrae are fused together using a bone graft. During spinal fusion, a perforated titanium cage may be surgically implanted within the space between two adjacent vertebrae after the pain-generating intervertebral disc is removed. The implanted spinal fusion cage must be appropriately sized to restore the normal disc height at the affected vertebral segment. The fusion cage is packed with bone graft, which grows through the perforated walls of the cage and eventually forms a solid bond or fusion with the adjacent vertebrae to prevent motion in the affected vertebral segment and reduces chronic discogenic pain.

Another approach for treating degenerative disc disease is total disc replacement ("TDR"), which seeks to alleviate discogenic pain, while maintaining or minimizing the loss of motion in the affected vertebral segment. During TDR, the pain-generating intervertebral disc is removed and a metallic artificial disc implant that allows motion, such as the Pro-Disc™-L manufactured by Synthes Spine of West Chester, PA and Charite® manufactured by DePuy Spine, Inc. of Raynham, Mass., is inserted into the space between the adjacent vertebrae. The TDR implant must be appropriately sized to restore the normal disc height at the affected vertebral segment, thereby reducing chronic discogenic pain, while maintaining or minimizing loss of range of motion in the affected vertebral segment.

While spinal fusion and TDR have been successfully used to treat degenerative disc disease, it is estimated that between 3-8% of these surgeries must be surgically revised. Some of these revisions are believed to be due to the improper selection, sizing and placement of the artificial disc or fusion cage, which is based predominantly on the judgment of the surgeon at the time of the procedure.

For example, surgeons today must rely on their experience and "feel" when using intervertebral spreaders or distractors to spread the affected intervertebral segment during TDR or fusion surgery. Both the artificial disc and fusion cage must fit in a "snug" intervertebral space that has appropriate ligament tension provided by the anterior longitudinal ligament, posterior longitudinal ligament (if it has not been removed), ligamentum flavum, facet capsular ligament (in the case of TDR where the facet is not removed), and the inter-transverse and inter-spinous ligaments. Too much distraction by the surgeon performing a TDR procedure will result in the placement of an implant that is too large for the intervertebral segment, reducing the ideal range of motion that the implant can provide. In contrast, insufficient ligament tension will not produce enough force on the endplates of the arthroplasty, resulting in loosening and ultimately subsidence (i.e., migration of the implant from its optimal position). Similarly, since fusion cages or devices should be placed in a stretched intervertebral segment for better fusion, insufficient ligament tension may result in an unsatisfactory fusion and/or undesired range of motion of the affected vertebral segment.

In addition, anterior and posterior pre- and post-distraction disc heights are important parameters for a surgeon to consider when placing an intervertebral disc arthroplasty. It is believed that there is an optimal window of anterior and posterior disc height that allows the optimal range of motion by the arthroplasty. Currently, surgeons must either "eyeball" anterior and posterior disc heights before and after distraction on a fluoroscope, and/or use so called "Yo-Yo" or trial devices to measure the size of the intervertebral space by forcing different Yo-Yo's into the space between adjacent vertebras until the correct sized Yo-Yo is placed. However, these Yo-Yo devices do not allow for ligament tension measurement and/or feel by the surgeon. Conventional intervertebral spreaders do not measure anterior and posterior disc heights.

Yet another parameter for a surgeon to consider when placing an intervertebral disc arthroplasty is the depth of the patient's vertebral endplate. New arthroplasties should cover the entire vertebral endplate outer-rim because this is where the strongest bone lies. However, neither conventional distractors/spreaders nor fluoroscopes provide a surgeon with the precise depth of the patient's vertebral endplate to select the correct size arthroplasty or fusion device that will cover the maximum amount of outer rim.

Intervertebral angle is also an important parameter that surgeons must estimate based on their experience using fluoroscopes and x-rays. Estimating the correct "lordotic" or "kyphotic" angle is important because it allows for the correct spinal segment alignment in the case of fusion devices, or for the maximum range of motion in the case of total disc arthroplasties. Conventional spreaders (distractors) or Yo-Yo devices do not provide for a precise determination of the intervertebral angle.

It is, therefore, desirable to reduce post-operative complications of spinal fusion and TDR arising from improper selection, sizing and placement of the artificial disc or fusion cage.

SUMMARY

In accordance with one aspect of this disclosure, a device and method are disclosed for intraoperatively and accurately measuring: (1) ligament tension while the surgeon is distracting (spreading) the affected intervertebral segment; (2) the anterior and posterior disc heights before and after distraction; (3) the vertebral endplate depth or distance; and (4) intervertebral angle during surgery.

In accordance with one aspect of this disclosure, a method is disclosed for determining an optimal size of an intervertebral implant to be inserted within an intervertebral space between two vertebrae in a patient. The method comprises inserting a distractor into the intervertebral space and measuring a vertebral endplate depth. The amount of force applied during distraction is measured with at least one transducer mounted on the distractor. The intervertebral space is distracted. The intervertebral angle and the posterior and anterior heights of the intervertebral space are measured. The optimal size of the intervertebral implant is selected corresponding to the measured vertebral endplate depth, posterior height, anterior height, and intervertebral angle.

In accordance with another aspect of this disclosure, a method is disclosed for determining an optimal size of an intervertebral implant to be inserted within an intervertebral space between two vertebrae in a patient. The method comprises inserting a distractor into the intervertebral space. The vertebral endplate depth is measured by moving a posterior rod on the distractor longitudinally to a position at the posterior margin of the vertebral endplate and moving an anterior rod on the distractor to a position at the anterior margin of the vertebral endplate. The force applied during distraction is measured using at least one transducer mounted on the distractor and the intervertebral space is distracted by rotating the posterior and anterior rods on the distractor until the measured force reaches a predetermined value. The posterior height of the intervertebral space is measured based on amount that the posterior rod is rotated and the anterior height of the intervertebral space is measured based on amount that the anterior rod is rotated. The intervertebral angle is measured based on the angular orientation of two pivotally connected handles on the distractor. The optimal size of the intervertebral implant is selected corresponding to the measured vertebral endplate depth, posterior height, anterior height, and intervertebral angle.

In accordance with another aspect of this disclosure, a device is disclosed for determining an optimal size of an intervertebral implant to be inserted within an intervertebral space between two vertebrae in a patient. The device comprises a first plate that is insertable within the intervertebral space for engagement with a first vertebral endplate and a second plate that is insertable within the intervertebral space for engagement with a second vertebral endplate. The first plate is operatively connected to a first handle and movable in response to movement of the first handle. The second plate is operatively connected to a second handle and movable in response to movement of the second handle. At least one transducer measures the force applied during distraction of the intervertebral space.

In accordance with another aspect of this disclosure, a device is provided for determining an optimal size of an intervertebral implant to be inserted within an intervertebral space between two vertebrae in a patient. The device comprises a movable posterior rod operatively connected to at least one posterior distracting member, the posterior distracting member being movable in a radial direction in response to rotation of the posterior rod. A movable anterior rod is operatively connected to at least one anterior distracting member, the anterior distracting member being movable in a radial direction in response to rotation of the anterior rod. At least one transducer is used to measure the force applied during distraction of the intervertebral space.

In accordance with another aspect of this disclosure, a device is disclosed for determining an optimal size of an intervertebral implant to be inserted within an intervertebral space between two vertebrae in a patient. The device comprises a movable posterior rod operatively connected to first and second posterior distracting members. The posterior distracting members are movable in opposing radial directions in response to rotation of the posterior rod, which includes markings corresponding to the distance that the posterior distracting members have moved for measuring posterior disc height. A movable anterior rod is operatively connected to first and second anterior distracting members. The anterior distracting members are movable in opposing radial directions in response to rotation of the anterior rod, which includes markings corresponding to the distance that the anterior distracting members have moved for measuring anterior disc height. The posterior and anterior rods are movable in a longitudinal direction, the anterior rod including a linear scale and the posterior rod including a position indicator for measuring the distance between the distal end of the posterior rod and the distal end of the anterior rod. The first posterior and anterior distracting members each having a terminal end that engages a first load sensor plate, the first load sensor plate being movable in response to movement of either the first posterior distracting member or the first anterior distracting member. The second posterior and anterior distracting members each having a terminal end that engages a second load sensor plate, the second load sensor plate being movable in response to movement of either the second posterior distracting member or the second anterior distracting member. A first handle is pivotally connected to a proximal end of the first load sensing plate and a second handle is pivotally connected to a proximal end of the second load sensing plate. The first and second handles are pivotally connected to one another and a protractor measures the angular orientation of the first and second handles. At least one transducer measures the force applied during distraction of the intervertebral space.

These and other advantages of the present disclosure will be apparent to those of ordinary skill in the art by reference to the following detailed description and the accompanying drawings.

DETAILED DESCRIPTION

Figure 1:
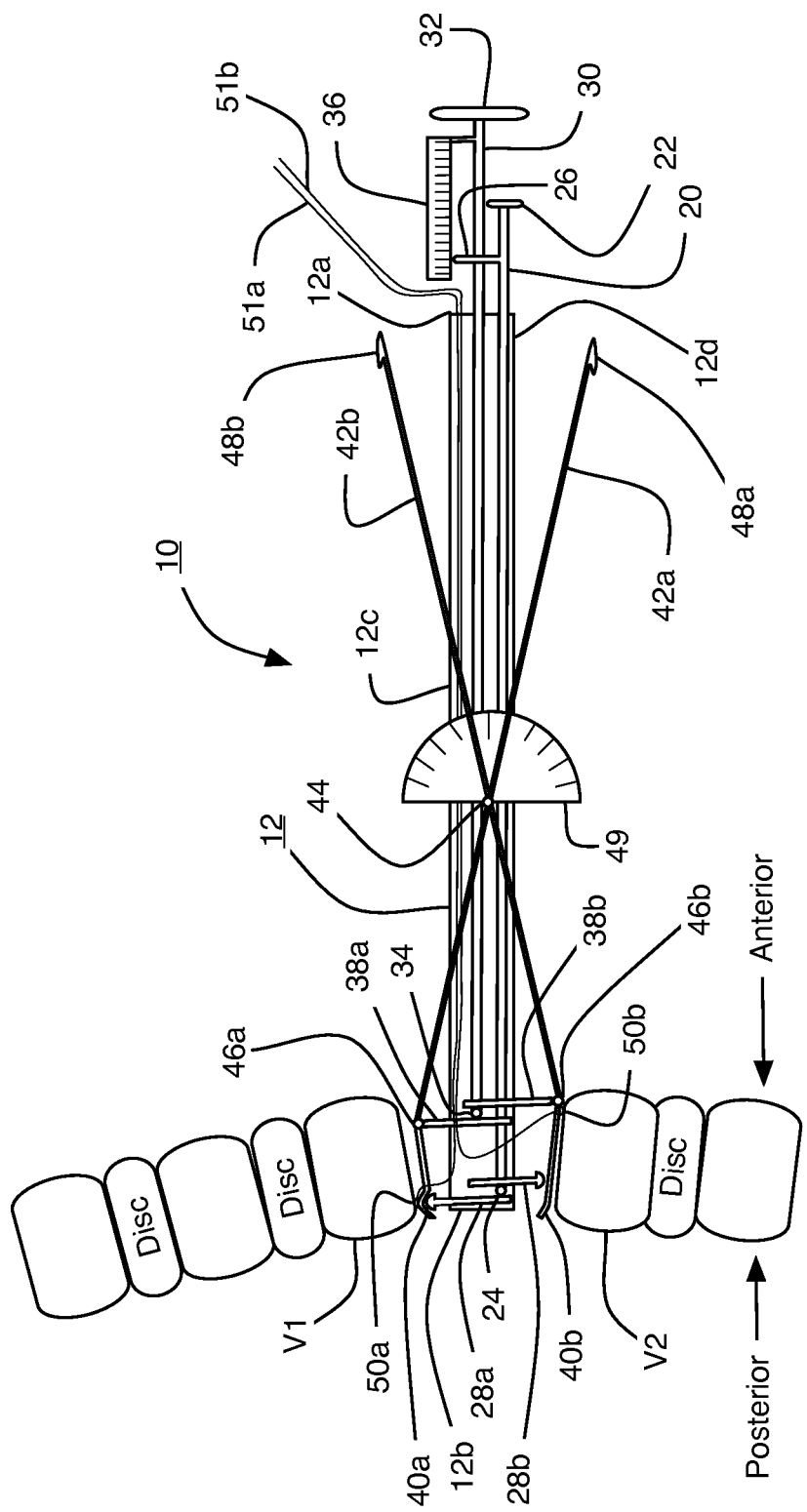
FIG. 1 is a side elevation view of a spinal measuring device and distractor in accordance with this disclosure.

Referring to FIG. 1, a measuring device and distractor 10 is shown in FIG. 1 inserted within the space between adjacent vertebrae V1, V2 after a pain-generating or diseased intervertebral disc is removed. Although the measuring device and distractor 10 is described herein as an intervertebral measuring device for selecting an optimal size arthroplasty for a patient undergoing a TDR or spinal fusion procedure, it is understood that the device 10 is not limited to use with this type of procedure and may be used in connection with a variety of other medical procedures, including, but not limited to, hip, knee and shoulder arthroplasty procedures.

The measuring device and distractor 10 preferably includes a housing 12. The housing 12 is preferably hollow and has a proximal end 12a and a distal end 12b. The housing 12 is preferably made from titanium, stainless steel or any other biologically suitable material that is safe for use within the body of a patient.

Two elongated rods—a posterior rod 20 and an anterior rod 30—are mounted within the housing 12 so that each rod may be rotated relative to and slide longitudinally within the housing. Each rod 20, 30 may, for example, be supported by one or more bearings or sleeves (not shown) mounted on the housing 12. One end of each rod 20, 30 preferably extends outwardly from the proximal end 12a of the housing 12 and terminates in a handle or knob 22, 32, which the surgeon may use to turn the rod or slide the rod longitudinally. The rods 20, 30 are preferably made from titanium, stainless steel or any other biologically suitable material that is safe for use within the body of a patient.

The opposing or distal end of the posterior rod 20 is coupled to and engages a pair of opposing posterior distracting members or pulls 28a, 28b. The posterior distracting members 28a, 28b project outwardly from the housing 12, preferably in a direction that is generally perpendicular to the longitudinal axis of the rod 20. The first posterior distracting member 28a preferably extends upwardly through the top 12c of the housing 12 in a direction toward the superior vertebrae V1 as illustrated in FIG. 1. The second posterior distracting member 28b preferably extends downwardly through the bottom 12d of the housing 12 in a direction toward the inferior vertebrae V2 as illustrated in FIG. 1. The top 12c and bottom 12d of the housing 12 are at least partially relieved to permit the distracting members 28a, 28b to extend outwardly therethrough and slide longitudinally with the posterior rod 20 as the rod is moved longitudinally relative to the housing 12.

The distracting members 28a, 28b are coupled to the distal end of the posterior rod 20 in a conventional manner that permits rod 20 to rotate relative to the distracting members 28a, 28b, while also permitting the distracting members 28a, 28b to move longitudinally with the posterior rod 20 as the rod is moved longitudinally relative to the housing 12.

The posterior rod 20 preferably includes a plurality of teeth about its circumference to form a gear (e.g., a circular pinion) at least in proximity to the location where the rod engages the distracting members 28a, 28b. The distracting members 28a, 28b also include a plurality of teeth on at least one surface to form a gear (e.g., a rack) for meshing engagement with the teeth (circular pinion) on the posterior rod 20 to convert rotational movement of the rod 20 into linear movement of the distracting members 28a, 28b toward or away from the adjacent vertebrae.

In other words, rotation of the posterior rod 20 in one direction will cause the first posterior distracting member 28a to extend or move upwardly through the top 12c of the housing 12 and simultaneously cause the second posterior distracting member 28b to extend or move downwardly through the bottom 12d of the housing. In contrast, rotation of the posterior rod 20 in the opposite direction will cause the first posterior distracting member 28a to retract or move downwardly into the top 12c of the housing 12 and simultaneously cause the second posterior distracting member 28b to retract or move upwardly into the bottom 12d of the housing.

Similarly, the opposing or distal end of the anterior rod 30 is coupled to and engages a pair of opposing anterior distracting members or pulls 38a, 38b. Like the posterior distracting members 28a, 28b, the anterior distracting members 38a, 38b also project outwardly from the housing 12, preferably in a direction that is generally perpendicular to the longitudinal axis of the rod 30.

Like the first posterior distracting member 28a, the first anterior distracting member 38a preferably extends upwardly through the top 12c of the housing 12 in a direction toward the superior vertebrae V1 as illustrated in FIG. 1. Like the second posterior distracting member 28b, the second anterior distracting member 38b preferably extends downwardly through the bottom 12d of the housing 12 in a direction toward the inferior vertebrae V2 as illustrated in FIG. 1. The top 12c and bottom 12d of the housing 12 are at least partially relieved to permit the distracting members 38a, 38b to extend outwardly therethrough and slide longitudinally with the anterior rod 30 as the rod is moved longitudinally relative to the housing 12.

The anterior distracting members 38a, 38b are coupled to the distal end of the anterior rod 30 in a conventional manner that permits rod 30 to rotate relative to the distracting members 38a, 38b, while also permitting the distracting members 38a, 38b to move longitudinally with the anterior rod 30 as the rod is moved longitudinally relative to the housing 12.

Like the posterior rod 20, the anterior rod 30 preferably includes a plurality of teeth about its circumference to form a gear (e.g., a circular pinion) at least in proximity to the location where the rod engages the anterior distracting members 38a, 38b. The distracting members 38a, 38b also include a plurality of teeth on at least one surface to form a gear (e.g., a rack) for meshing engagement with the teeth (circular pinion) on the anterior rod 30 to convert rotational movement of the rod 30 into linear movement of the distracting members 38a, 38b toward or away from the adjacent vertebrae.

In other words, rotation of the anterior rod 30 in one direction will cause the first anterior distracting member 38a to extend or move upwardly through the top 12c of the housing 12 and simultaneously cause the second anterior distracting member 38b to extend or move downwardly through the bottom 12d of the housing. In contrast, rotation of the anterior rod 30 in the opposite direction will cause the first anterior distracting member 38a to retract or move downwardly into the top 12c of the housing 12 and simultaneously cause the second anterior distracting member 38b to retract or move upwardly into the bottom 12d of the housing.

A plurality of spaced apart graduations (not shown) are preferably provided near the proximal end of each rod 20, 30 to provide a visual indication of and correspond to the distance that the distracting members 28a, 28b, 38a, 38b are displaced as the rod is rotated in use. In this manner, the device 10 may be used to measure the anterior and posterior disc heights before and after intervertebral distraction to aid the surgeon in selecting the correct sized arthroplasty or fusion device for the spine of the patient undergoing the procedure. Like the rods 20, 30, the distracting members 28a, 28b, 38a, 38b are preferably made from titanium, stainless steel or any other biologically suitable material that is safe for use within the body of a patient.

A ruler or linear scale 36 having a plurality of spaced apart graduations or markings is preferably mounted on or otherwise connected to the anterior rod 30 in proximity to the handle 32. A position indicator 26 is preferably mounted on or otherwise connected to the posterior rod in proximity to the handle 22. As the rods 20, 30 are moved longitudinally relative to one another, the distance between the distal end of the posterior rod 20 and the distal end of the anterior rod 30 is indicated by particular graduation on the ruler 36 that is aligned with the position of the position indicator 26. In this manner, the device 10 may be utilized to measure the depth of the vertebral endplate to select the correct sized arthroplasty or fusion device that will cover the maximum amount of the outer rim of the vertebral endplate.

The end of the first posterior and anterior distracting members 28a, 38a that extends out of the top 12c of the housing 12 engages a superior side load sensor plate 40a, which is shown adjacent to the superior vertebrae V1 in FIG. 1. The end of the distracting members may include a rounded head as is shown at the end of distracting member 28a. The proximal end of the superior side load sensor plate 40a is pivotally connected via a hinge or pin 46a to the distal end of a first scissor member, lever or link 42a, which terminates at its proximal end with a handle 48a.

Similarly, the end of the second posterior and anterior distracting members 28b, 38b that extends out of the bottom 12d of the housing 12 engages an inferior side load sensor plate 40b, which is shown adjacent to the inferior vertebrae V2 in FIG. 1. The end of the distracting members may include a rounded head as is shown at the end of distracting member 28b. The proximal end of the inferior side load sensor plate 40b is pivotally connected via a hinge or pin 46b to the distal end of a second scissor member, lever or link 42b, which terminates at its proximal end with a handle 48b. The two scissor members 42a, 42b and pivot pins 44, 46a, 46b may be made from aluminum, stainless steel, titanium or any other suitable material that is biologically safe for use in medical procedures.

The two scissor members 42a, 42b intersect and are pivotally connected to one another via pin or hinge 44 to form a scissor-like configuration. When the handles 48a, 48b are squeezed or otherwise moved toward one another by the surgeon, the scissor members 42a, 42b pivot about pin 44 causing the distal ends of the scissor members (and the pivotally connected load sensor plates 40a, 40b) to spread or otherwise move away from each other.

A semi-circular protractor 49 having a plurality of spaced apart graduations or markings is positioned on the housing 12 proximate to the pivot pin 44 to measure the angular orientation of the two scissor members 42a, 42b. This angular orientation corresponds to the angular orientation or intervertebral angle of affected vertebral endplates when the handles 48a, 48b are squeezed together to pivot the load sensor plates 40a, 40b against the endplates of the superior and inferior vertebrae V1, V2. In this manner, the device 10 may be used to determine the intervertebral angle, which will provide for the correct spinal segment alignment in the case of fusion devices or for the maximum range of motion in the case of TDR.

A transducer 50a, 50b that converts force into a measurable electrical output, such as a conventional low-profile load sensor or load cell, is preferably mounted on each load sensor plate 40a, 40b to measure ligament tension when the surgeon is distracting (spreading) the affected intervertebral segment V1, V2 using the device 10. The transducer may be constructed from stainless steel or other biologically safe material. The transducer 50a, 50b may be bonded or otherwise attached to the load sensor plate 40a, 40b in a conventional manner. Each transducer 50a, 50b is preferably coated or covered with a thin layer of sterile plastic or other biologically safe material to protect the sensor and maintain sterility.

Wiring 51a, 51b, such as conventional shielded cabling, provides an electrical connection between the transducer 50a, 50b and a display (not shown) that provides signal processing and a visual indication of the force (preferably in Newtons) being applied by the device 10 during distraction of the affected vertebral segment V1, V2. The wiring 51a, 51b preferably extends from the sensor 50a, 50b through the housing 12 and out the proximal end 12a of the housing, where the wiring may be connected to the display. In this manner, the device 10 may be used to measure ligament tension and aid the surgeon in determining whether the appropriate amount of tension is being applied during distraction (spreading) of the intervertebral segment.

The measuring device and distractor 10 may be used by a surgeon as follows to selecting an optimal size arthroplasty for a patient undergoing a TDR or spinal fusion procedure. First, the patient may be positioned in a supine, neutral position on an operating table. Using an anterior approach, the surgeon exposes and removes the degenerative or diseased intervertebral disc, leaving a hollow intervertebral disc space between the adjacent vertebrae V1, V2.

Figure 2:
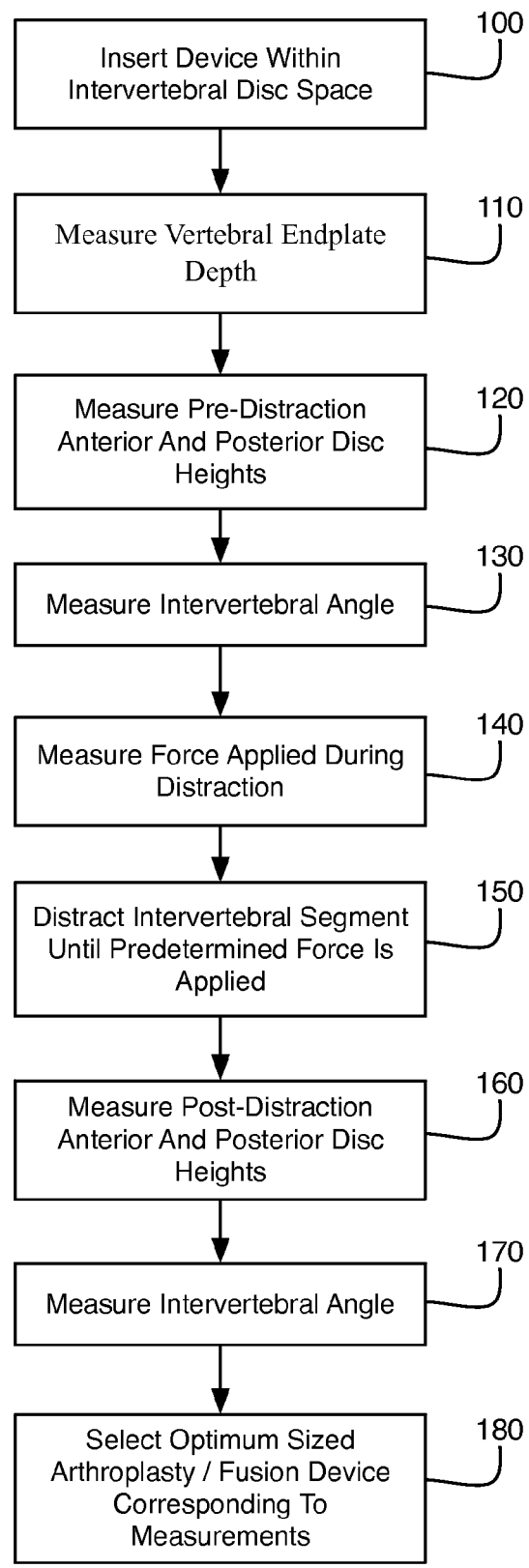
FIG. 2 is a flow chart illustrating a preferred sequence of steps for determining an optimal size of an intervertebral implant to be inserted within an intervertebral space between two vertebrae in a patient.

Referring to FIG. 2, in step 100, the measuring device and distractor 10 is then inserted intraoperatively within the body of the patient until the distal end 12b of the housing 12 is positioned within the intervertebral disc space at the affected vertebral segment. The distracting pulls 28a, 28b, 38a, 38b should be sufficiently retracted to avoid interference with the vertebral endplates.

In step 110, the vertebral endplate distance or depth is then measured by sliding the posterior rod 20 longitudinally until the distracting member 28a is positioned at the posterior edge or margin of the vertebral endplate. The anterior rod 30 is then moved longitudinally until the distracting member 38b is positioned at the anterior edge or margin of the vertebral endplate. The endplate depth corresponds to the particular graduation on the ruler 36 on the anterior rod 30 that is aligned with the position indicator 26 on the posterior bar 20. Knowing the vertebral endplate depth will allow the surgeon to select the optimal sized arthroplasty or fusion device that will cover the maximum amount of the outer rim of the vertebral endplate. The posterior and anterior rods 20, 30 may optionally be locked in place within the housing 12 to restrict longitudinal movement of the bars, while permitting rotational movement.

Next, the surgeon will measure the pre-distraction anterior and posterior disc heights using the device 10 in step 120. To measure the posterior disc height, the surgeon will grasp the handle 22 and turn the posterior rod 20, causing the first and second posterior distracting members 28a, 28b to move outwardly until the respective load sensor plates 40a, 40b contact the posterior edge of the vertebral endplates. The posterior disc height corresponds to the particular graduation on the circumference of the posterior rod 20 indicating the amount of rotation of the rod.

Similarly, to measure the anterior disc height, the surgeon will grasp the handle 32 and turn the anterior rod 30, causing the first and second anterior distracting members 38a, 38b to move outwardly until the respective load sensor plates 40a, 40b contact the anterior edge of the vertebral endplates. The anterior disc height corresponds to the particular graduation on the circumference of the anterior rod 20 indicating the amount of rotation of the rod.

The surgeon may also measure the intervertebral angle in step 130 by squeezing the handles 48a, 48b on the proximal end of scissor members 42a, 42b. This causes the scissor members 42a, 42b to pivot about pivot pin 44 until the respective load sensor plates 40a, 40b contact the vertebral endplates. The angular orientation of the two scissor members 42a, 42b is then measured using the graduations on the protractor 49, which corresponds to the angular orientation or intervertebral angle of affected vertebral endplates. In this manner, the device 10 may be used to determine the intervertebral angle, which will provide for the correct spinal segment alignment in the case of fusion devices or for the maximum range of motion in the case of TDR.

After the pre-distraction measurements are taken, the surgeon may distract (spread) the intervertebral segment in step 150 by turning the posterior and anterior rods 20, 30, which causes the distracting members 28a, 28b, 38a, 38b to move outwardly. The transducers 50a, 50b located on the load sensor plates 40a, 40b measure the amount of force or tension being applied to the ligaments during distraction in step 140, which the surgeon can monitor on a display electrically connected to the transducers via wires Ma, Mb. In step 150, the surgeon stops distracting the intervertebral segment when the desired tension is indicated on the display. This will minimize or eliminate circumstances where insufficient or excessive tension is applied to the ligaments during distraction, resulting in improper sizing of the arthroplasty or fusion device for the particular patient.

When the desired ligament tension is attained and distraction discontinued, the surgeon then uses the device 10 to measure the post-distraction posterior and anterior disc heights (step 160) and intervertebral angle (step 170) in the manner indicated above. The device 10 is then removed from the patient and, in step 180, the surgeon may use the measured endplate depth or distance, the pre- and post-distraction posterior and anterior disc heights, and the pre- and post-distraction intervertebral angle to select the optimal sized arthroplasty or fusion device for the particular patient undergoing the TDR or spinal fusion procedure.

Having described and illustrated the principles of this application by reference to one or more preferred embodiments, it should be apparent that the preferred embodiment(s) may be modified in arrangement and detail without departing from the principles disclosed herein and that it is intended that the application be construed as including all such modifications and variations insofar as they come within the spirit and scope of the subject matter disclosed herein.

What is claimed is:

1. A device for determining an optimal size of an intervertebral implant to be inserted within an intervertebral space between two vertebrae in a patient, comprising:
    a first plate operatively connected to a first handle and movable in response to movement of the first handle, the first plate insertable within the intervertebral space for engagement with a first vertebral endplate;
    a second plate operatively connected to a second handle and movable in response to movement of the second handle, the second plate insertable within the intervertebral space for engagement with a second vertebral endplate; and
    at least one transducer for measuring the force applied during distraction of the intervertebral space;
    wherein the first handle is a movable posterior rod and the second handle is a movable anterior rod,
    the posterior rod operatively connected to first and second posterior distracting members, the posterior distracting members being movable in opposing radial directions in response to rotation of the posterior rod, and
    the anterior rod operatively connected to first and second anterior distracting members, the anterior distracting members being movable in opposing radial directions in response to rotation of the anterior rod.

2. The device according to claim 1, wherein the first posterior and anterior distracting members each have a terminal end that engages the first plate, the first plate being movable in response to movement of either the first posterior distracting member or the first anterior distracting member.

3. The device according to claim 2, wherein the second posterior and anterior distracting members each have a terminal end that engages the second plate, the second plate being movable in response to movement of either the second posterior distracting member or the second anterior distracting member.

4. The device according to claim 3, wherein the posterior rod includes markings corresponding to the distance that the posterior distracting members have moved for measuring posterior disc height.

5. The device according to claim 3, wherein the anterior rod includes markings corresponding to the distance that the anterior distracting members have moved for measuring anterior disc height.

6. The device according to claim 1, wherein the posterior and anterior rods are movable in a longitudinal direction, the anterior rod including a linear scale and the posterior rod including a position indicator for measuring the distance between the distal end of the posterior rod and the distal end of the anterior rod.

7. The device according to claim 1, further comprising:
    a first lever pivotally connected to a proximal end of the first plate and a second lever pivotally connected to a proximal end of the second plate, the first and second levers pivotally connected to one another; and
    a protractor for measuring the angular orientation of the first and second levers.

8. The device according to claim 1, wherein the transducer is mounted on the first plate.

9. The device according to claim 8, further comprising a second transducer mounted on the second plate.

10. The device according to claim 1, wherein the posterior rod includes a plurality of teeth defining a gear and the posterior distracting members each include a plurality of teeth on at least one surface thereof for meshing engagement with the teeth on the posterior rod such that rotation of the posterior rod causes the posterior distracting members to move in opposing radial directions.

11. The device according to claim 10, wherein the anterior rod includes a plurality of teeth defining a gear and the anterior distracting members each include a plurality of teeth on at least one surface thereof for meshing engagement with the teeth on the anterior rod such that rotation of the anterior rod causes the anterior distracting members to move in opposing radial directions.

* * * * *